(12) United States Patent
Suzuki et al.

(10) Patent No.: US 6,582,603 B1
(45) Date of Patent: *Jun. 24, 2003

(54) METHOD FOR PURIFYING THROMBIN SUBSTRATE AND/OR INHIBITORS OR METHOD FOR ELIMINATING THE SAME

(75) Inventors: Toyoaki Suzuki, Tokyo (JP); Kazuya Hosokawa, Kawasaki (JP); Masanori Nagata, Tokyo (JP)

(73) Assignee: Fujimori Kogyo Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/529,963

(22) PCT Filed: Oct. 23, 1998

(86) PCT No.: PCT/JP98/04812

§ 371 (c)(1),
(2), (4) Date: Jul. 21, 2000

(87) PCT Pub. No.: WO99/20655

PCT Pub. Date: Apr. 29, 1999

(30) Foreign Application Priority Data

| Oct. 23, 1997 | (JP) | 9-309398 |
| Mar. 6, 1998 | (JP) | 10-55559 |
| Jun. 8, 1998 | (JP) | 10-159687 |

(51) Int. Cl.$^7$ ............................................. B01D 15/08
(52) U.S. Cl. ........................ 210/635; 210/656; 530/383; 530/389.3; 530/413; 435/214
(58) Field of Search ...................... 210/635, 656, 210/659, 198.2; 435/214; 530/387.1, 389.3, 413, 417, 383

(56) References Cited

U.S. PATENT DOCUMENTS

| 5,840,499 A | * 11/1998 | Brass .................... 530/387.1 |
| 5,939,304 A | * 8/1999 | Suzuki et al. ............... 435/214 |
| 6,024,936 A | * 2/2000 | Coughlin .................. 530/389.3 |

FOREIGN PATENT DOCUMENTS

| JP | A-58-10522 | 1/1983 |
| JP | A-59-167519 | 9/1984 |

OTHER PUBLICATIONS

Ashton, R.W., et al., "Preparation and Characterization of Anhydrothrombin", Biochemistry, vol. 34, No. 19, pp. 6454–6463 (1995).

* cited by examiner

Primary Examiner—Ernest G. Therkorn
(74) Attorney, Agent, or Firm—Woodbridge & Associates, PC; Richard C. Woodbridge, Esq; Stuart H. Nissim, Esq.

(57) ABSTRACT

A method for the refinement of a thrombin substrate, characterized by comprising therein a step of affinity chromatography formed by using an affinity adsorbent having as a ligand a thrombin or thrombin analogue deprived of nucleophilicity (activity) without causing stereostructure to the linkage with a substrate is disclosed.

3 Claims, 1 Drawing Sheet

FIG. 1

METHOD FOR PURIFYING THROMBIN SUBSTRATE AND/OR INHIBITORS OR METHOD FOR ELIMINATING THE SAME

REFERENCE TO RELATED APPLICATIONS

This application is a 371 of PCT/JP98/04812 filed Oct. 23, 1998.

TECHNICAL FIELD

This invention relates to an affinity adsorbent possessing as a ligand a thrombin or thrombin analogue deprived of nucleophilicity (nucleophilic activity) without causing stereostructure to the linkage with a substrate, affinity chromatography formed by using the affinity adsorbent, and further a method for the refinement of a novel thrombin substrate characterized by comprising therein a step of working the affinity chromatography. More particularly, this invention relates to a method for the refinement of a thrombin substrate by using as a ligand for affinity chromatography a thrombin or thrombin analogue deprived of nucleophilicity (nucleophilic activity) without causing stereostructure to the linkage with such a substrate as anhydrothrombin. Further, this invention relates to a method for the elimination of a thrombin substrate contained as an extraneous matter in some other substance subjected to refinement by utilizing the specific adsorbing-desorbing activity of the affinity chromatography.

BACKGROUND ART

The blood coagulation factor VIII (FVIII) participates in the endogenous mechanism of the first phase of blood coagulation from the start of blood coagulation until before the formation of thrombin in the mechanism of blood coagulation. Since the disease due to the deterioration of this FVIII activity is called hemophilia A, the FVIII factor is referred to as antihemophilic globulin or antihemophilic factor A.

The hemophilia A is a recessive inheritance of sex chromosome and is sorted by the degree of deterioration of factor activity into three classes, light illness, medium illness, and serious illness. The patients of light illness rarely suffer spontaneous hemorrhage and, even when they do, they barely conceive of this symptom by personally experiencing difficulty in attaining hemostasis in connection with injury, surgical operation, or extraction of teeth. The patients of medium to serious illness suffer spontaneous hemorrhage as a main symptom and, owing to the obstruction to the endogenous coagulation, sustain this hemorrhage in the depths of tissue. Particularly, the intra-articular hemorrhage characterizes this disease and, when suffered to occur repeatedly, induces arthritis, compels the joints to develop contractual deformation and eventually manifest inevitable functional obstruction, and shows discernible signs of intramuscular hemorrhage, intracranial hemorrhage, and renal hemorrhage.

Though the gene therapy or the transplantation therapy is conceivable for the cure of a patient of hemophilia, it is still on the stage of undergoing a clinical study at present. It has not yet been put to use on patients of hemophilia. In this state of things, it is necessary to effect the cure by replenishing the patient with the FVIII, a factor depleted on the occurrence of a hemorrhage, in an effort to stop the hemorrhage or make this replenishment preparatorily in expectation of the hemorrhage.

As the FVIII preparation for the cure of a patient of hemophilia (by heightening the level in the blood of the depleted FVIII up to the level fit for hemostasis and preventing the blood flow), the cryoprecipitate (allowing the presence of FVIII at a high concentration), a precipitate which occurs when the Chon I fraction in a frozen state is gradually dissolved at a low temperature, is pharmaceutically prepared and used because the concentration of FVIII in the human blood plasma is so low as to fall in the range of 0.1 to 0.2 mg/lit. Since the transfusion of this preparation has the possibility of exposing the patent to infection with hepatitis B or hepatitis C or AIDS (acquired immunodeficiency syndrome), such heated preparations of very high safety as the dry concentrated human coagulant factor VIII preparations which has been dried by heating at 60° C. for 10 hours, and the dry concentrated human coagulant factor VIII which has been dried by heating at 65° C. for 95 hours, are now in use. Besides, the dry concentrated human coagulant factor VIII which has been produced by subjecting the donor's blood plasma as a raw material to a heat treatment or a treatment with an organic solvent/surfactant (as the treatment with TNBP/Octoxynol 9) thereby inactivating viruses possibly entrained by the plasma and separating the resultant coagulant in a refined state by the use of an anti-FVIII monoclonal antibody and the recombinant preparation which is produced, as disclosed in JP-A-07-278,197 (U.S. Pat. No. 2,513,993), by refining a product obtained by the gene recombination technique as by affinity chromatography using a monoclonal antibody to the VIII:C factor active C-terminal subunit have been similarly finding utility.

Even the preparations which have been endowed with heightened safety by the inactivation of viruses due to the heat treatment or the treatment with an organic solvent/surfactant cannot allow perfect denial of the possibility of exposing the patients who have used the preparation to such virus infectious as non-A or non-B type hepatitis. In the case of the heated preparations, since they contain fibrinogen, their administration has the possibility of excessively increasing the fibrinogen concentration in the patients' blood. Then, in the case of the recombinant preparation separated in a refined state by the use of the aforementioned monoclonal antibody, (1) the preparation has the possibility of including a heterogenous animal protein because the monoclonal antibody more often than not uses the heterogenous animal protein and (2) even from the viewpoint of cost, the preparation eventually obtained becomes inevitably expensive.

The coagulant factor XIII (hereinafter referred to simply as "FXIII") participates in the formation of a stable fibrin polymer which constitutes itself the final stage of the mechanism of blood coagulation. Hence, it is called a fibrin stabilizing factor. The FXIII normally occurs in an inactive state in the blood plasma. When the blood plasma forms thrombin in consequence of hemorrhage, the FXIII is activated with thrombin and calcium ion and consequently enabled to stabilize the fibrin. In the case of a patient who has been depleted slightly or seriously of the FXIII, therefore, the FXIII which displays a normal value during the coagulation of blood manifests such phenomena as secondary hemorrhage because the fibrin clots consequently formed are not stable. Clinically, therefore, the FXIII preparations are widely used for promoting the cure of wounds.

The FXIII conventionally used domestically has originated in the placenta. Owing to the charge with the complaints ① that the state of inclusion of the FXIII differs in the placenta and in the blood plasma, ② that the FXIII has the possibility of including such an impurity as transforms ultimately into an immunogen, and ③ that the relevant process of inactivation of virus has a problem (JP-A-01-250,326), it has altered the origin to the blood plasma. Since the blood plasma contains the FXIII only in a minute amount, however, the FXIII preparation has relied on the imported blood plasma for its source.

The FXIII preparation is extracted from the bloodplasma, the blood platelets, and the placenta, separated in a refined state, and pharmaceutically prepared by pasteurization (a treatment of liquid heating at 60° C. for 10 hours) which inactivates various viruses (retroviruses such as hepatitis B virus and HIV-1). It is otherwise obtained by producing a recombinant FXIII (including an analogue thereof which has a blood coagulating activity) in the yeast cells by the technique of gene recombination and then, for the purpose of pharmaceutical preparation, separating the produced recombinant FXIII in a refined state from the supernatant covering the ruptured yeast cells. The main methods which are available for the manufacture of the FXIII in the refined state from the blood plasma, the blood platelets, the placenta, or the recombinant FXIII are varying combinations of precipitation and gel permeation using ammonium, acrynol, alcohol, trisodium citrate, or glycine as disclosed in ① Loewy, A. G., Journal of Biological Chemistry, 236, 2625 (1961), ② Janusuzko, B. T., Nature, 191, 1093 (1961), ③ Bohn V. H., Blut, 25, 235 (1972), and ④ Winkelman L., et. al, Thrombosis and Haemostasis, 55, 402 (1986). The produced FXIII preparations have assays in the approximate range of 15–50%.

The protein C (hereinafter occasionally abbreviated as "PC" for simplicity) is a vitamin K-dependent glycoprotein, i.e. one species of α-carboxyglutamic acid-containing protein. In the presence of a thrombomodulin in the hemandioendothelic surface layer, the PC is activated by the thrombin and converted into an activated protein C (hereinafter occasionally abbreviated as "APC" for simplicity). The APC is a species of serine protease, which inactivates factor V (VF and FVa) and factor VIII (FVIII and FVIIIa) and exhibits a strong anticoagulating activity. It is known to liberate a plasminogen activator from the vascular wall and promote fibrinolysis (the APC also exhibits a fibrinolysis promoting activity because it joins with a tPA inhibitor and represses the tPA inhibiting activity of the inhibitor). Further, the protein C depletion is known to manifest a serious symptom of thrombosis and this fact clearly demonstrates that the APC forms an important control factor for the system of coagulant fibrinolysis. Thus, the PC or the APC is expected to allow development of new preparations as an anticoagulation agent and a fibrinolytic agent.

It has been heretofore known that the amount of the PC present in the blood plasma or the amount of the PC induced in the system of tissue culture is very small. (The PC which is present in the blood plasma, for example, is synthesized in the liver and is circulated in the form of an enzyme precursor through the blood plasma at a concentration of about 4 $\mu$g/ml.) For the purpose of safely using the protein C or the activated protein C extensively as an anticoagulation agent and a fibrinolytic agent, it is very important to separate the PC or the APC in a refined state.

The following methods may be cited as means for producing the APC from the blood. They are (1) a method which comprises deriving a purified protein C from the human blood plasma by means of affinity chromatography using an antiprotein C antibody, activating this purified protein C with a human thrombin, and then purifying the activated protein C by cation chromatography [Blood, 63, p. 115–121 (1984)], (2) a method which comprises deriving a protein C in a refined state from the human blood plasma by a Kisiel's process of adsorbing barium citrate from the human blood plasma, eluting the adsorbate, fractionating the eluate with ammonium sulfate, and passing the relevant fraction through the steps of DEAE-Sephadex column chromatography, dextran agarose sulfate chromatography, and polyacryl amide gel electrophoresis and then activating the purified protein C into the APC [Journal of Clinical Investigation, 64, p. 761–769 (1979)], and (3) a method which comprises activating a commercially available protein C-containing blood coagulating preparation by a Taylor et al's method [Journal of Clinical Investigation, 79, p. 918–925 (1987)] into the APC.

The method of (1) mentioned above, however, has the problem that the antiprotein C antibody itself to be used in the affinity chromatography is extremely expensive, the protein C is produced by the affinity chromatography with a low yield of about 30%, and the APC preparation eventually obtained is inevitably very expansive. Then, the method of (2) mentioned above has the problem that the process for the separation of the protein C in the refined state has numerous steps and the procedure of separation in the refined state is complicated, that the refinement to a high degree is difficult because this method, unlike the method of (1) mentioned above, does not resort to the specific adsorption and desorption of the protein C, that the protein C is produced with a low yield of about 30%, and that the finally produced APC preparation is inevitably very expensive.

As means for manufacturing the APC by the use of the technique of gene recombination, the methods disclosed in JP-A-61-205,487, JP-A-01-2,338, and JP-A-01-85,084, for example, may be cited. The protein C produced as described above or the raw material for the activated protein C are separated in the refined state by combining standard biochemical method of separation and refinement. As concrete examples of the combination, a salt-out method using ammonium sulfate, an ion-exchange chromatography using an ion-exchange resin, a gel permeation method, and an electrophoretic method may be cited.

Even in the case of the method for effecting the separation by combining standard biochemical processes of separation and refinement, similarly in the case of the method of (2) above, the process for refinement and separation of the PC or the APC consumes a long time and the procedure of refinement and separation is complicated and, not similarly in the case of the method of (1) which resorts to specific adsorption and desorption of the PC or the APC, the refinement to a high degree is attained only with difficulty and the PC or the APC is purified with a low yield of about 30%.

For the manufacture of such thrombin substrates as blood coagulant factor V, blood coagulant factor XI, protein S, heparin cofactor II, fibrinogen, and thrombin receptor as well as for the manufacture of the PC or the APC mentioned above, methods for effecting separation and refinement by combining standard biochemical processes of separation and refinement have been finding utility. For the purpose of enabling thrombin substrates to be produced stably in high purity with high efficiency, these products have the same problems as the PC or the APC mentioned above.

The present inventors have carried out a diligent study on thrombin substrates with a view to fulfilling the objects of this invention and consequently have discovered that the incorporation in a process for purifying a thrombin substrate (including the case of making this incorporation at the end of the final step in the process of refinement) of the affinity chromatography effected by using as a ligand capable of specifically and reversibly reacting with the thrombin substrate a thrombin such as, for example, anhydrothrombin deprived of nucleophilicity (activity) without causing stereostructure to the linkage with the substrate permits solution of the problems mentioned above in consequence of the separation as with the anhydrothrombin because the anhydrothrombin is a protein of human origin manufactured from a human thrombin and is decisively inexpensive as compared with the antiprotein C antibody. This invention has been perfected as a result. The present inventors have further discovered that the activity manifested by the anhydrothrombin in specifically separating the thrombin substrate can be applied to the elimination of a thrombin substrate (optionally two or more species of substrate) contained as an foreign matter in some other substance subjected to refinement. This invention has been perfected as a result.

Specifically, an object of this invention is to provide an affinity adsorbent possessing as a ligand a thrombin or thrombin analogue deprived of nucleophilicity (activity) without causing stereostructure to the linkage with a substrate and affinity chromatography effected by using the affinity adsorbent.

A further object of this invention is to provide a method for efficiently, safely, and stably refining a thrombin substrate at a low cost with a high assay owing to the use of a novel and inexpensive means of separation and refinement fulfilled by a simple procedure of separation and refinement and a process consisting of a small number of steps.

A further object of this invention is to provide a method for refining FVIII inexpensively without suffering the product of refinement to entail the possibility of including therein such impurities as heterognous animal protein.

Another object of this invention is to provide a method for refining FVIII without entailing such virus infections as hepatitis (hepatitis B and hepatitis C) and AIDS (acquired immunodeficiency syndrome) or suffering the administration thereof to induce an undue increase of the concentration of fibrinogen in the blood.

A further object of this invention is to provide a method for allowing the FXIII contained only in a small amount in the blood plasma to be refined with a high assay at a high ratio of recovery as compared with the conventional refining method.

Yet another object of this invention is to provide a method which allows the FXIII derived from the FXIII of such natural origins as the blood platelets and the placenta instead of the blood plasma to be refined with a high assay at a high ratio of recovery as compared with the conventional refining method while entailing practically no possibility of suffering the product of refinement to include therein such an impurity as grows into an immunogen, a problem encountered by the conventional refining method, and allowing a marked decrease of the probability of viral inclusion.

Still another object of this invention is to provide a method for enabling even the FXIII obtained by the procedure of gene recombination and the mutant thereof (the mutant comprising the amino acid sequence of FXIII having at least one of the amino aids thereof depleted or substituted by the procedure of gene recombination and possessing an FXIII activity) to be refined with a high assay at a high ratio of recovery as compared with the conventional refining method which effects separation and refinement of such impurities as proteins by utilizing the method for refining the FXIII of natural origin.

DISCLOSURE OF THE INVENTION

The method for refining a thrombin substrate according to this invention is characterized by comprising therein a step of affinity chromatography effected by using an affinity adsorbent having as a ligand a thrombin or thrombin analogue deprived of nucleophilicity (activity) without causing stereostructure to the linkage with the substrate.

Specifically, this invention has originated in a resolution aimed at developing a specific method for refining a thrombin substrate by the affinity chromatography using as a ligand an inexpensive protein of human origin yet to be uncovered, carried out by a diligent study continued with a view to obtaining as a key for the development an inexpensive ligand of human origin capable of being adsorbed to and desorbed from the thrombin substrate, and concluded with the discovery that a thrombin or thrombin analogue deprived of activity without causing stereostructure to the linkage with the substrate is useful for the development. This invention has perfected as a result.

The term "thrombin substrate" as used in this invention refers to what functions as a substrate for the thrombin. As concrete examples thereof, thrombin substrates such as fibrinogen (blood coagulant factor I), blood coagulant factor VIII, blood coagulant factor XIII, blood coagulant factor V, blood coagulant factor XI, protein C, protein S, and thrombin receptor may be cited. In accordance with Michaelis-Menten's theory (the theory that an enzymatic reaction advances as a chemical reaction after an enzyme molecule and a substrate molecule are combined to form an enzyme substrate complex and the complex liberates the reaction product and causes the enzyme to revert to the state which existed at the initial stage of the reaction), the thrombin substrate undergoes a reaction of the form represented by the following formula ①.

Thrombin+Thrombin substrate⇌Thrombin·thrombin substrate complex→Thrombin+activated thrombin substrate     ①

It is said that the charge relay system of the amino acid in the proximity of the active serine in the thrombin (The term "the charge relay system" refers to the series of hydrogen bonds between the side chains of the amino acids existing at the sites of activity of the chymotrypsin and other serine proteases and this system forms the cause for the nucleophilicity (activity) of high degree of the hydroxyl groups of the serine residues at the sites of activity. The series of hydrogen bonds allow flow of electrons from the negatively charged carboxyl group of the aspartic acid to the hydroxyl group of the serine residue and, as a result, impart nucleophilicity of high degree to the oxygen of the hydroxyl group.) participates in the nucleophilicity (activity) of the thrombin.

This charge relay system, when ruptured by anhydrodization or gene manipulation, is enabled to bring marked deterioration of the nucleophilicity (activity) without causing stereostructure to the linkage with the thrombin substrate. For example, the marked deterioration of the activity (nucleophilicity) of thrombin is attained without causing stereostructure to the linkage with a thrombin substrate by substituting asparagine for the aspartic acid in the site of thrombin activity or by substituting alanine for the active serine in the thrombin. This fact demonstrates that the thrombin or thrombin analogue deprived of nucleophilicity (activity without causing stereostructure to the linkage with the thrombin substrate undergoes a reversible reaction of the form represented by the following formula ② with thrombin substrates such as fibrinogen (blood coagulant factor I), blood coagulant factor V, blood coagulant factor VIII, blood coagulant factor XI, blood coagulant factor XIII, protein C, protein S, thrombin receptor and other proteins (providing that the case of using anhydrothrombin as a thrombin or thrombin analogue deprived of activity (nucleophilicity) without causing stereostructure to the linkage with a thrombin substrate will be cited herein by way of example). To be specific, the anhydrothrombin which is deprived of thrombin activity without causing stereostructure to the linkage with a thrombin substrate by causing a thrombin to react with a synthetic inhibitor thereby forming an ester bond with the active serine residue of the thrombin retains an ability to bind itself with such a carrier (supporting member) as Sepharose and, owing to the specific binding ability with the thrombin substrate, manifests an outstanding binding property. It has been demonstrated that this specific ability can be utilized in a great measure as a ligand for an affinity adsorbent. This anhydrothrombin, in spite of the use of an enzyme as a raw material, may well be regarded as a ligand of new concept which allows exclusive utilization of the specific binding ability thereof.

The plan for selectively recovering a thrombin substrate by using as a ligand a thrombin or thrombin analogue deprived of nucleophilicity (activity) without causing stereostructure to the linkage with the substrate of the anhydrothrombin mentioned above and causing the thrombin substrate to be specifically adsorbed on the ligand can be carried through by an extremely simple procedure resembling the standard procedure of affinity chromatography. Specifically, the selective recovery of the thrombin substrate as a target substance is accomplished by preparing a solution containing the target substance at a proper salt concentration in a proper pH range, passing the solution through a column using a carrier (adsorbent) having the ligand fixed thereon, then washing the column with a proper buffer solution, and subsequently passing an eluting solution through the column thereby allowing the target substance adsorbed on the column to be desorbed in a sharp peak. Thus, the effect aimed at can be attained. Incidentally, the solution containing the thrombin substrate as a target substance must be kept in advance in a state containing no thrombin substrate other than the target substance or in a state containing the thrombin substrate other than the target substance only in a very minute amount. The reason for this necessity is that the thrombin substrate other than the target substance has the possibility of being specifically adsorbed on the anhydrothrombin serving as the ligand. Though this necessity brings no particular problem for the separation and refinement of the thrombin substrate subsequent to the production thereof by the technique of gene recombination, it demands due respect in the case of separating and refining the target substance from the blood plasma of human origin. When protein C is to be separated and refined from the blood plasma of human origin, for example, the protein C can be easily separated from the blood coagulant factor VIII, the blood coagulant factor XIII, etc. by subjecting the blood plasma to a procedure of adsorption-desorption with barium citrate.

As the initial stage of refinement, several thrombin substrates may be refined or eliminated from a plurality of protein solutions.

As the thrombin deprived of nucleophilicity (activity) without causing stereostructure to the linkage with the substrate mentioned above, the anhydrothrombin which is obtained by anhydrodizing a human thrombin proves useful.

The anhydrothrombin of this nature can be synthesized by the following methods.

(1) A method for the synthesis of anhydrothrombin, comprising the following steps and performing them sequentially in the order mentioned.

1. a step of causing the active serine residue site of a thrombin to react with a synthesis inhibitor,
2. a step of subjecting the resultant reaction product to an alkali treatment at a pH of not less than 11, and
3. a step of carrying out a work of recovery, and characterized by allowing the presence of at least one compound selected from the group consisting of polyhydric alcohols and saccharides and a salt or an amphoteric electrolyte at least at the step for performing the work of recovery.

(2) A method for the synthesis of anhydrothrombin according to (1) above, wherein at least one compound selected from the group consisting of polyhydric alcohols and saccharides is at least one compound selected from the group consisting of glycerin, ethylene glycol, and sucrose.

(3) A method for the synthesis of anhydrothrombin according to (1) or (2) above, wherein the salt or the amphoteric electrolyte is at least one compound selected from the group consisting of sodium chloride, potassium chloride, and glycine.

(4) A method for the synthesis of anhydrothrombin according to any of (1)–(3) above, wherein at least one compound selected from the group consisting of polyhydric alcohols and saccharides, in an atmosphere having an air temperature of 23° C. and a relative humidity of 50%, accounts for a proportion of not less than 5% to the whole amount of the product undergoing the work of recovery in gravimetric ratio when the compound is a liquid or in volumetric ratio when the compound is powder, granules, or a solid body.

(5) A method for the synthesis of anhydrothrombin according to any of (1)–(4) above, wherein the concentration of the salt or the amphoteric electrolyte is not less than 0.2 M.

The method for the synthesis of anhydrothrombin mentioned above comprises 1. a step of causing the active serine residue cite of a thrombin to react with a synthesis inhibitor (first step),
2. a step of subjecting the product of reaction to an alkali treatment at a pH of not less than 11 (second step), and
3. a step of performing a work of recovery (third step), and performs these steps sequentially in the order mentioned, and is characterized by allowing the presence of at least one compound selected from the group consisting of polyhydric alcohols and saccharides and a salt or an amphoteric electrolyte at least at the step for performing the work of recovery.

Figure 1:
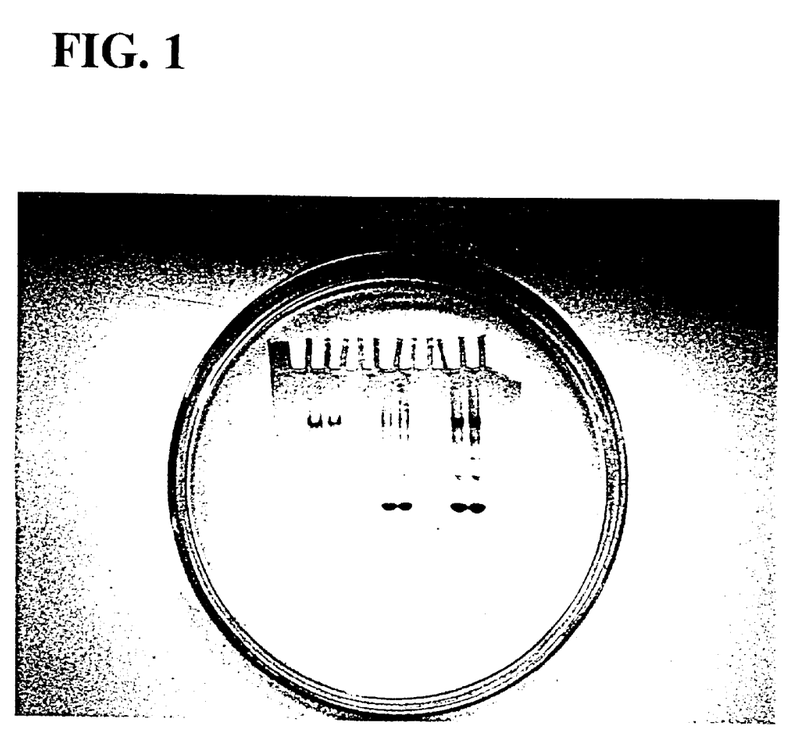
FIG. 1 is a photograph which, in the place of a drawing, represents the results of an experiment of electrophoresis performed on the FXIII which was finally obtained by refinement in Example 1 as a preferred embodiment of this invention.

Specifically, in the case of using phenyl methane sulfonyl fluoride (hereinafter referred to as "PMSF") as the synthesis inhibitor, for example, the method can be expressed by the following reaction formula. A typical synthesis according to this specific example is schematically illustrated in FIG. 1.

Serine residue of α-thrombin

PMS-thrombin → Anhydrothrombin

Now, the method for the synthesis of anhydrothrombin mentioned above will be explained below along the flow of the first through third steps mentioned above.

(1) First Step

The first step consists in causing the active serine residue cite of a thrombin to react with a synthesis inhibitor for the purpose of depriving the thrombin of the activity thereof by the reaction of the thrombin with the synthesis inhibitor and the consequent formation of an ester bond with the active serine residue of the thrombin. This inactivation of the thrombin can be attained by using the known methods such as, for example, the method reported in literature (Biochemistry 1995, 34, 6454–6463) and the methods enumerated in Table 1 below as well.

Table 1 schematically illustrates a method for the production of anhydrothrombin, one species of thrombin deprived of nucleophilicity (activity) without causing stereostructure, to be used in the method for refinement of FXIII according to this invention.

TABLE 1

| Method reported in Biochemistry 1995, 34, 6454–6463 | Method disclosed in patent application 09-148,116 |
| --- | --- |
| α-Thrombin/50 mM phosphate buffer 0.1M NaCl 0.1% PEG ↓ | α-Thrombin/50 mM phosphate buffer 0.1M NaCl ↓ |
| Addition of PMSF ↓ | Addition of PMSF ↓ |
| Exchange of buffer solution in Sephadex column ↓ | Gel permeation ↓ |
| Concentration with YM10 membrane ↓ | Addition of 1M NaOH and subsequent 12 minutes' reaction ↓ |
| Addition of 6N Gdn-HCl/6N NaOH ↓ 10 minutes' agitation | Standing in 1M Tris-50% glycerin of pH 8.2 at 4° C. for 12 hours |
| Addition of 0.4M phosphate buffer, pH 6 ↓ | ↓ Dialysis performed for 12 hours ↓ |
| Dropwise addition to phosphate buffer containing 0.75M NaCl, 0.1% PEG ↓ | Concentration with YM10 membrane ↓ |
| Concentration with YM10 membrane ↓ 20 hours' retention Readdition of PMSF ↓ | Affinity chromatography in benzamidine-Sepharose column ↓ Measurement of protein content of fractionated liquid |
| Exchange of buffer solution in Sephadex column ↓ | Elimination of dialyzed benzamidine |
| Affinity chromatography in Benzamidine-Sepharose column ↓ Measurement of protein content of fractionated liquid Elimination of dialyzed benzamidine | |
| Total: About 72 hours | Total: About 43 hours |

Incidentally, the species of thrombin which can be used or the synthesis of the anhydrothrombin mentioned above does to need to be particularly restricted but may be suitably selected from among various commercially available species of refined thrombin such as, for example, the thrombin of Cohn Paste III (of human origin), the refined thrombin (of bovine origin) made by Mochida Pharmaceutical Co., Ltd., and the refined thrombin (of human origin) made by Midori Juji K. K., which are usable in their unmodified form.

The synthesis inhibitor which can be used for the synthesis of anhydrothrombin mentioned above imposes no particular restriction and requires only to be capable of forming an ester bond by reacting with the active serine residue of thrombin as represented by the reaction formula (1) mentioned above. As concrete examples of the synthesis inhibitor usable herein, various sulfonyl fluorides such as PMSF, 2-phenylethane-1-sulfonyl fluoride, methane sulfonyl fluoride, and p-toluene sulfonyl (tosyl) fluoride, and tosyl chloride, diisopropyl fluorophosphoric acid (hereinafter occasionally referred to as "DFP"), 3,4-dichloroisocoumarin (hereinafter occasionally referred to as "3,4-DCI"), L-1-chloro-3-[4-tosylacid]-7-amino-2-heptanon-hydrochloric acid (hereinafter occasionally referred to as "TLCK"), and L-1-chloro-3-[4-tosylacid]-4-phenyl-2-butanone (hereinafter occasionally referred to as "TPCK") may be cited.

When such a synthetic inhibitor is to be added, it may be dissolved in advance in such a solvent as, for example, acetone, methanol, acetone, ethanol, propanol, isopropanol, butanol, propan-2-ol, dimethyl formamide, or dimethyl sulfoxide. In the addition of the synthetic inhibitor, due attention is requested to be paid to the necessity of lowering the thrombin activity to not more than 3%, preferably to not more than 1%, for the sake of allaying the complexity of the work of separating and removing a possible excess of the synthetic inhibitor and heightening the reactivity of the added inhibitor.

The reaction solvent, for the sake of favoring the survival of the thrombin, is only required to be a salt solution incorporating therein Nacl or a salt solution further incorporating therein several species of ions such as $K^+$, $Ca^{2+}$ and $Mg^{2+}$ for the purpose of adjusting the osmotic pressure and the ion balance, and to be a buffer solution arbitrarily selected from among buffer solutions exhibiting pH values of 2–10, preferably 4–8 for the purpose of stably retaining the pH value. As concrete examples of the buffer solution usable for the addition to the reaction solvent, phosphate buffer solution, carbonate buffer solution, bicarbonate buffer solution, tris buffer solution, citric acid-sodium phosphate buffer solution, succinic acid-sodium hydroxide buffer solution, potassium phthalate-sodium hydroxide buffer solution, imidazole-hydrochloride buffer solution, borate buffer solution, physiological salt solution, and Good's buffer solution may be cited.

As regards the reaction conditions, since a thermal change generally affects seriously the stabilization of thrombin, the reaction temperature is preferred to be in the range of −30 to 50° C., preferably 4–40° C.

The product obtained by the reaction mentioned above is refined and separated by using any of the known methods. The method to be used for the refinement and separation does not need to be particularly restricted but may be suitably selected from among gel permeation, ion-exchange chromatography, affinity chromatography, ultrafiltration, and dialysis, for example. To explain the gel permeation as a typical method, by adding the solution resulting from the reaction to a column of gel (such as, for example, Sephadex, Biogel, or Agarose gel) particles swelled in advance with a solvent and continuing the passage of a solvent through the column, first the thrombin product as a high molecular solute and subsequently the synthesis inhibitor as a low molecular solute are eluted and the separation of the two solute is automatically effected. The solvent which can be used herein, for the sake of favoring the survival of the thrombin, is only required to be a salt solution incorporating therein NaCl or a salt solution further incorporating therein several species of ions such as $K^+$, $Ca^{2+}$ and $Mg^{2+}$ for the purpose of adjusting the osmotic pressure and the ion balance, and to be a buffer solution arbitrarily selected from among buffer solutions exhibiting pH values of 2–10, preferably 4–8 for the purpose of stably maintaining the pH value. As concrete examples of the buffer solution usable herein, phosphate buffer solution, carbonate buffer solution, bicarbonate buffer solution, tris buffer solution, citric acid-sodium phosphate buffer solution, succinic acid-sodium hydroxide buffer solution, potassium phthalate-sodium hydroxide buffer solution, imidazole-hydrochloride buffer solution, borate buffer solution, physiological salt solution, and Good's buffer solution may be cited.

(2) Second Step and Third Step

At the second and third steps anhydrothrombin is synthesized by dissociating the ester bond and exchanging the serine residue for an alanine residue, and the step of performing an alkali treatment at a pH of not less than 11 on the thrombin product refined and separated at the first step (second step) and the work of recovery (third step) are carried out sequentially in the order mentioned for the purpose of obtaining the anhydrothrombin with a high yield by a simple procedure without causing coagulation-association during the course of the regeneration due to the return of the pH value from a high pH region to the vicinity of neutrality. The method comprising these three steps is characterized by allowing the presence of at least one compound selected from the group consisting of polyhydric alcohols and saccharides and a salt or an amphoteric electrolyte at least at the step for performing the work of recovery.

First, the solvent for dissolving the thrombin product refined and separated at the first step, for the sake of favoring the survival of the thrombin, is only required to be a salt solution incorporating therein NaCl or a salt solution further incorporating therein several species of ions such as $K^+$, $Ca^{2+}$ and $Mg^{2+}$ for the purpose of adjusting the osmotic pressure and the ion balance, and to be a buffer solution arbitrarily selected from among buffer solutions exhibiting pH values of 2–10, preferably 4–8 for the purpose of stably maintaining the pH value. As concrete examples of the buffer solution usable herein, phosphate buffer solution, carbonate buffer solution, bicarbonate buffer solution, tris buffer solution, citric acid-sodium phosphate buffer solution, succinic acid-sodium hydroxide buffer solution, potassium phthalate-sodium hydroxide buffer solution, imidazole-hydrochloride buffer solution, borate buffer solution, physiological salt solution, and Good's buffer solution may be cited.

At least one compound selected from the group consisting of polyhydric alcohols and saccharides and used in the synthesis of the anhydrothrombin is added, in combination with a salt or an amphoteric electrolyte, for the purpose of promoting the anhydrodization without causing coagulation-association of protein during the alkali treatment in a high pH region and enabling the anhydrothrombin to be regenerated without causing coagulation-association during the return of the pH value from a high region to the vicinity of neutrality in the procedure of recovery. It should be noted that the object of the synthesis of the anhydrothrombin mentioned above can be attained by using at least one compound exclusively in the procedure of recovery.

As concrete examples of at least one compound selected from the group consisting of polyhydric alcohols and saccharides mentioned above, polyhydric alcohols (inclusive of sugar alcohols) such as tetrytols (specifically erythritol, D-threitol, L-threitol, and D,L-threitol), pentitols (specifically ribitol, D-arabinitol, L-arabinitol, D,L-arabinitol, and xylitol), hexitols (specifically allitol, dulcitol (galactitol), sorbitol (D-glucitol), L-glucitol, D,L-glucitol, D-mannitol, L-mannitol, D,L-mannitol, D-altritol, L-altritol, D,L-altritol, D-iditol, and L-iditol), heptitol, maltitol, lactitol, glycerin, ethylene glycol, diethylene glycol, triethylene glycol, propylene glycol, dipropylene glycol, 1,3-butylene glycol, neopentyl glycol, pentamethylene glycol, hexamethylene glycol, pentaerythritol, dipentaerythritol, tripentaerythritol, trimethylol ethane, trimethylol propane, anhydrous enneaheptitol, 1,4-butane diol, 1,2,4-butane triol, and 1,2,6-hexane triol, and saccharides such as glycerin aldehyde dioxane acetone, threose, erythrulose, erythrose, arabinose, ribulose, ribose, xylose, xylulose, lyxose, glucose, fructose, mannose, idose, sorbose, gulose, talose, tagatose, galactose, allose, psicose, altrose, and sucrose may be cited. These compounds may be used either singly or in the form of a mixture of two or more members. Among other compounds cited above, at least one compound selected from the group consisting of glycerin, ethylene glycol, an sucrose proves particularly advantageous.

Preferably, at least one compound selected from the group consisting of polyhydric alcohols and saccharides mentioned above air an atmosphere having an air temperature of 23 ° C. and a relative humidity of 50%, accounts for a proportion of not less than 5%, preferably not less than 15%, to the whole amount of the product of recovery in gravimetric ratio when the compound is a liquid or in volumetric ratio when the compound is powder, granules, or a solid body. It is provided, however, that even when the proportion to the whole amount is less than 5%, the second and third steps can be effectively carried out and the effect aimed at can be efficiently manifested by relatively heightening the concentration of the salt or the amphoteric electrolyte to be used in combination. Thus, the proportion (concentration) of at least one compound selected from the group consisting of polyhydric alcohols and saccharides mentioned above to the whole amount of the product of recovery is preferred to be suitably decided so as to ensure efficient manifestation of the effect aimed at. This decision requires due consideration to be paid to the kind and concentration of the salt or the amphoteric electrolyte to be used in combination with at least one compound mentioned above.

The salt or the amphoteric electrolyte to be used in the synthesis of the anhydrothrombin mentioned above is added, in combination with at least one compound selected from the group consisting of polyhydric alcohols and saccharides mentioned above, for the purpose of promoting the anhydrodization without causing coagulation-association of protein during the alkali treatment in a high pH region and enabling the anhydrothrombin to be regenerated without causing coagulation-association during the return of the pH value from a high region to the vicinity of neutrality in the procedure of recovery. The salt or the amphoteric electrolyte imposes no particular restriction but requires only to be capable of affording a salt concentration (ionic strength) or dielectric constant fit for acquiring the object. The choice between an organic and an inorganic is not critical for the compound under discussion.

As concrete examples of the salt or the amphoteric electrolyte mentioned above, alkali metal halogenides such as sodium chloride and potassium chloride, alkaline earth metal halogenides such as magnesium chloride and calcium chloride, inorganic acid salts such as ammonium chloride, ammonium sulfate, sodium carbonate, potassium carbonate, magnesiumcarbonate, ammoniumcarbonate, calciumcarbonate, sodium hydrogen carbonate, potassium hydrogen carbonate, potassium hydrogen carbonate, ammonium hydrogen carbonate, sodium phosphate, disodium hydrogen phosphate, potassium dihydrogen phosphate, ammonium dihydrogen phosphate, sodium borate, and potassium borate, organic acid salts such as sodium citrate, potassium citrate, magnesium citrate, calcium citrate, ammonium citrate, sodium phthalate, potassiumphthalate, magnesiumphthalate, calciumphthalate, ammonium phthalate, sodium succinate, potassium succinate, magnesium succinate, calcium succinate, ammonium succinate, sodium acetate, potassium acetate, calcium acetate, magnesium acetate, and ammonium acetate, and water-soluble salts or amphoteric electrolytes of amines fated to form such amphoteric electrolytes as glycine and alanine may be cited. These compounds may be used either singly or in the form of a mixture of two or more members. Among other compounds mentioned above, alkali metal salts, inorganic salts, and amphoteric electrolytes of low molecular weights which are easily soluble in water, easily adjustable to the optimum ionic strength (salt concentration) and dielectric constance, depending on the concentration of at least one compound selected from the group consisting of polyhydric alcohols and saccharides and allowed to coexist thereof, and easily susceptible of (or capable of simplifying) the step of refinement and separation (such as dialysis) prove particularly preferable. Specifically, at least one compound selected from the group consisting of sodium chloride, potassium chloride, and glycine may well be called a satisfactory choice.

The concentration of the salt or the amphoteric electrolyte mentioned above is properly not less than 0.2 M, preferably not less than 0.5 M. It is provided, however, that even when this concentration is less than 0.2 M, the second and third steps can be effectively carried out and the effect aimed at can be efficiently manifested by relatively heightening the proportion of the salt or the amphoteric electrolyte to the whole amount of the product of recovery, similarly to the case of at least one compound selected from the group consisting of polyhydric alcohols and saccharides mentioned above.

The anhydrodization by the treatment with an alkali at the second step is attained by adding the alkali so as to adjust the pH of the reaction system to a level of not less than 11 (when necessary, in the presence of at least one compound selected from the group consisting of polyhydric alcohols and saccharides mentioned above in combination with a salt or an amphoteric electrolyte) keeping the reaction temperature in the range of −30 to 50° C., preferably 4−40° C. If the pH mentioned above is less than 11, the shortage will bring the disadvantage of preventing the occurrence of the reaction for removal of PMSF and obstructing the advance of the anhydrodization. As concrete examples of the alkali mentioned above, monovalent salts such as sodium hydroxide and potassium hydroxide, divalent bases such as calcium hydroxide, bariumhydroxide, calciumoxide, magnesiumoxide, calcium carbonate, and sodium carbonate and trivalent bases such as iron hydroxide may be cited. If the reaction temperature mentioned above is less than −30° C., the shortage will bring the disadvantage of possibly freezing the reaction system. Conversely, if it exceeds 50° C., the excess will bring the disadvantage of suffering the thrombin to succumb to degeneration of protein and preventing the degenerated thrombin from reverting to the original state by a subsequent operation of regeneration.

Then, at the third step, the solution containing the anhydrothrombin synthesized by the aforementioned treatment with the alkali is subsequently (after undergoing the reaction for anhydrodization) is caused to revert to the original state (the state of stereostructure) by the operation of regeneration performed in the presence of at least one compound selected from the group consisting of polyhydric alcohols and saccharides mentioned above in combination with a wait or an amphoteric electrolyte. The operation of regeneration mentioned above does not impose any particular restriction but requires only to make use of any of the methods known heretofore. For example, a method which comprises adjusting the pH of the system (solution) resulting from the reaction in the range of 4−10 with a solvent (the same solvent as used in the aforementioned reaction of anhydrodization may be used) and allowing the treated system to stand for a prescribed period at a temperature in the range of −30 to 50° C. and a method which comprises adjusting the pH in the range of 4−10 by dialysis are available for the regeneration.

Then, the regenerated anhydrothrombin is subjected to the work of refinement and separation which is aimed at removing at least one compound selected from the group consisting of polyhydric alcohols and saccharides and served the purpose of the presence in the reaction system and optionally further removing the salt or the amphoteric electrolyte (the salt or the amphoteric electrolyte such as, for example, NaCl or phosphate occasionally does not need to be elaborately removed when the eluting solution to be finally used for the work of extracting the anhydrothrombin tolerates the presence thereof). The method for the refinement and separation of this nature does not need to be particularly restricted but may be suitably selected from among the methods known heretofore such as, for example, dialysis, ultrafiltration, gel chromatography, ion-exchange chromatography, and affinity chromatography. In the typical work of dialysis, at least one compound selected from the group consisting of polyhydric alcohols and saccharides is separated from the regenerated anhydrothrombin solution by dialysis across a membrane of cellulose through the medium of a solvent at a pH in the range of 4−10 (the same solvent as used in the reaction of anhydrodization or the operation of regeneration may be adopted).

Then, the target anhydrothrombin is obtained by performing the work of refinement and separation which is aimed at the removal of impurities. The method for effecting the refinement and separation does not need to be particularly restricted but may be selected arbitrarily from among the methods known heretofore. For example, a method which, as schematically illustrated in FIG. 1, comprises concentrating the solution of anhydrothrombin excluding at least one compound selected from the group consisting of polyhydric alcohols and saccharides by the use of a YM membrane, then passing the concentrated solution through a benzamidine-Sepharose column equilibrated with a solvent of a pH of 4−10 (the same solvent as used for the reaction of anhydrodization or the operation of regeneration mentioned above may be used) thereby cleaning the solution, further eluting the adsorbate with a benzamidine solution adjusted to a pH of 4−10 (the solution is allowed to contain such salts as sodium chloride, potassium chloride, calcium chloride, or magnesium chloride for the purpose of attaining specific adsorption of the target protein), and dialyzing the resultant eluate with a solvent of a pH of 4−10 (the same solvent as used for the reaction of anhydrodization and the operation of regeneration mentioned above may be used) for the purpose of removing benzamidine thereby accomplishing the extraction of the target anhydrothrombin solution and a method which resorts to separation by ultrafiltration or to gel permeation with a Sephadex column may be adopted.

The anhydrothrombin which is synthesized by some other method than the methods described above such as, for example, a method which uses guanidine hydrochloride (Gdn-HCl) in the place of PMS during the course of the reaction may be suitably used.

This invention further relates to an affinity adsorbent which possesses as a ligand a thrombin or thrombin analogue deprived of nucleophilicity (activity) without causing stereostructure to the linkage with a substrate. As the thrombin which is deprived of nucleophilicity (activity) without causing stereostructure to the linkage with a substrate, the anhydrothrombin mentioned above proves advantageous. Alternatively, the thrombin which is deprived of nucleophilicity (activity) without causing stereostructure to the linkage with a substrate may be a mutant of thrombin which is formed of an amino acid sequence of thrombin having at least one of the amino acids thereof depleted, substituted, or added by the manipulation of gene recombination and deprived of nucleophilicity (activity) without causing stereostructure to the linkage with a substrate instead of the anhydrothrombin mentioned above. Though the site of linkage of thrombin with a thrombin substrate has not yet been perfectly elucidated, it is suspected that the site which is called the anion binding site of thrombin plays an important part. Thus, the refinement of a thrombin substrate is attained by a thrombin which has been deprived of nucleophilicity (activity) without sacrificing the binding site or causing stereostructure. It is, therefore, permissible to use this mutant of thrombin as a ligand for the affinity adsorbent of this invention.

As respects the use of this mutant of thrombin, the mutant of thrombin which has been deprived of nucleophilicity (activity) without causing stereostructure to the linkage with a substrate by depletion, substitution, or addition of an amino acid residue which is through to be endowed with the nucleophilicity (activity) of thrombin by a charge relay system can be used. The thrombin which is deprived of nucleophilicity (activity) without causing stereostructure to the linkage with a substrate can be obtained, for example, by substituting the aspartic acid in the site of thrombin activity by asparagine or substituting the active serine in the site of thrombin activity by alanine.

This invention is further aimed at providing an affinity chromatograph which is formed by using an affinity adsorbent which possesses as a ligand a thrombin or thrombin analogue deprived of nucleophilicity (activity) without causing stereostructure to the linkage with a substrate. The thrombin analogue deprived of nucleophilicity (activity) without causing stereostructure to the linkage with the substrate mentioned above is preferred to be a mutant of thrombin which is formed of an amino acid sequence having at least one of the amino acids thereof depleted, substituted, or added by the manipulation of gene recombination. The thrombin deprived of nucleophilicity (activity) without causing stereostructure to the linkage with a substrate is preferred to be anhydrothrombin.

As regards the construction of an affinity adsorbent and the method for the production of the affinity adsorbent (such as, for example, the selection of a carrier and the method for production thereof, the presence or absence of the necessity for a spacer, the selection of the mode for solidification of a ligand, the method (reaction) for the solidification of the ligand, and the concentration of the solidified ligand) other than the ligand, varying known techniques are widely available for arbitrary selection.

The thrombin substrate which can be subjected to the method of refinement contemplated by the present invention is allowed to embrace a wide variety of factors which participate in the blood coagulation system. As concrete examples of the factor under discussion, such factors as protein C which serve as substrates for thrombin may be cited in addition to such factors as blood coagulant factor VIII, blood coagulant factor XIII, blood coagulant factor V, and blood coagulant factor XI.

As concrete examples of the thrombin substrate which can be subjected to the method of refinement mentioned above, thrombin substrates of human origin such as blood plasma, blood platelets, and placenta and thrombin substrate s obtained by the manipulation of gene recombination (this invention is further allowed to embrace mutants which are formed of an amino acid sequence of a thrombin substrate having at least one of the amino acids thereof depleted, substituted, or added by the manipulation of gene recombination and which retain a blood coagulating activity and an antithrombin activity respectively) may be cited. The method for manufacturing the thrombin substrate by the use of the technique of gene recombination does not need to be particularly restricted but may be arbitrarily selected from among a wide variety of relevant processes of the known techniques of gene recombination. Concerning the manufacture of activated protein C, for example, the activated protein C which is manufactured by a method similar to the method disclosed in JP-A-61-205,487, JP-A-01-2,338, or JP-A-01-85,084 may be cited. Alternatively, the activated protein C may be obtained by preparing a protein C by the use of the technique of gene recombination mentioned above, refining this protein C by the method of refinement according to this invention, and then activating the refined protein C. The method for activating the protein C into the activated protein C has no particular restriction. The activation can be executed, for example, by a method which attains the activation with a thrombin separated from the human blood or the bovine blood or a method which effects the activation with an equivalent protease.

Further, this invention contemplates incorporating in the process for the refinement of a thrombin substrate a process of affinity chromatography formed by using as a ligand a thrombin or thrombin analogue deprived of nucleophilicity (activity) without causing stereostructure to the linkage with the substrate mentioned above. The choice of the particular stage at which the incorporation is made in the process for the refinement of the thrombin substrate may be suitable decided in accordance with the known method of refinement as by finding through a preliminary experiment the stage that fits the purpose of accomplishing the object and obtaining the product most efficiently with a high yield.

Further, this invention also embraces an aspect which is characterized by incorporating in the process for the elimination of a thrombin substrate contained as a foreign matter a process of affinity chromatography formed by using as a ligand a thrombin or thrombin analogue deprived of nucleophilicity (activity) without causing stereostructure to the linkage with the substrate mentioned above. This aspect of the invention consists in applying the aforementioned step of refinement and separation. In due respect of the special quality manifested by the anhydrothrombin, a ligand for the affinity chromatography, in specifically adsorbing and desorbing a thrombin substrate, the present invention contemplates utilizing the affinity chromatography for effecting ready separation and removal of a thrombin substrate (such as, for example, fibrinogen) which has found a way as a foreign matter into some other substance subjected to refinement. The explanation on the anhydrothrombin which is a ligand for the affinity chromatography and on the thrombin substrate is the same as that which has been already furnished with respect to the method of refinement above and will be omitted here.

BEST MODE OF EMBODYING THE INVENTION

EXAMPLE 1

Production of Affinity Adsorbent, Affinity Chromatography, and Method for Refinement To a solution having 52.1 mg of α-thrombin of Cohn Paste III origin dissolved in 10 ml of a 5 mM phosphate buffer/0.1 M NaCl/pH 6.5, 30 μl of a methanol 7% phenyl methane sulfonyl fluoride (PMSF) solution was each added at intervals of minutes until total activity reached a level less than 1%. This solution was cooled to 0° C. and then left reacting for 12 minutes with 0.05 ml of 1 M NaOH added thereto. To the reaction product, 5 ml of an aqueous 3M NaCl solution was added and 19 g of glycerin was further added.

The resultant solution was adjusted to pH 7.8 by the use of a 1 M tris hydrochloride buffer solution/50% glycerin/pH 7 and left standing at 4° C. for 12 hours. Thereafter, the solution was dialyzed into a 50 mM tris hydrochloride buffer solution/1 M NaCl/pH 7.5 and further dialyzed into a 50 mM tris hydrochloride buffer solution/0.1 M NaCl/pH 7.5. The resultant solution was added to a benzamidine Sepharose column equilibrated in advance with a 50 mM tris hydrochloride buffer solution/0.1 M NaCl/pH 7.5. The impurity peak was thoroughly washed with the same buffer solution and the adsorbate was eluted with a 50 mM tris hydrochloride buffer solution/0.1 M NaCl/0.2 M benzamidine/pH 7.5. The solution resulting from the desorption was deprived of benzamidine by dialysis with a 50 mM tris hydrochloride buffer solution/1 M NaCl/pH 7.5. The produced anhydrothrombin, 28 mg in weight, was immobilized on a NHS-activated column (made by Farmacia Corp) to obtain anhydrothrombin Sepharose, an affinity adsorbent.

A solution of a FXIII preparation (made by Hoechst and sold under the trademark designation of "Fibrogamin P") in a 50 mM tris hydrochloride buffer solution/0.2 M NaCl/pH 7.5 was passed through the column equilibrated in advance with the same buffer solution. Further, the impurities were thoroughly washed by an operation of graduation with NaCl and the adsorbate was eluted with a 50 mM tris hydrochloride buffer solution/0.2 M NaCl/0.2 M benzamidine/pH 7.5. The first fraction, 15 ml in volume, of the peak of benzamidine was recovered and used as the FXIII solution. The solution was recovered with an yield of not less than 80% and subjected to electrophoresis to obtain a single band having a molecular weight (Mr) of 320000. FIG. 2 is a photograph which illustrates the electrophoresis in the place of a drawing.

EXAMPLE 2

An aqueous solution containing a FXIII solution obtained from human blood plasma by the method disclosed in JP-A-01-250,326 was dialyzed against a 50 mM tris hydrochloride buffer solution/0.1 M NaCl/pH 7.5. The solution consequently obtained was passed through an anhydrothrombin column which was the same as the column used in Example (1) equilibrated in advance with the same buffer solution. Further, the impurities were thoroughly washed by an operation of graduation using 0.1–1M NaCl and the adsorbate was eluted with a 50 mM tris hydrochloride buffer solution/0.2 M NaCl/0.2 M benzamidine/pH 7.5. The solution was recovered with a yield of about 80% and was subjected further to electrophoresis to afford a single band having Mr of 320000.

EXAMPLE 3

A FXIII solution obtained from the human blood plasma by the method reported in Winkelman L. et al., Thrombosis and Haemostasis, 55, 402 (1986) was dialyzed against a 50 mM tris hydrochloride buffer solution/0.2 M NaCl/pH 7.5 and then passed through an anhydrothrombin column (the same column as used in Example 1) equilibrated in advance with the same buffer solution. Further, the impurities were thoroughly washed by an operation of graduation with 0.1–1 M NaCl and the adsorbate was eluted with a 50 mM tris hydrochloride buffer solution/0.2 M NaCl/0.2 M benzamidine. The solution was recovered with a yield of about 80% and was further subjected to electrophoresis to afford a single band having Mr of 320000.

EXAMPLE 4

A solution of 1000 U of a blood coagulant factor VIII obtained by gene recombination (made by Baxter Corp and sold under the trademark designation of "Reconate") in 10 ml of a 50 mM tris hydrochloride buffer solution/0.2 M NaCl/0.1 M $CaCl_2$/pH 7.5 was passed through a column packed with the anhydrothrombin obtained in Example 1.

The column was washed with four times the column volume of the same buffer solution and the adsorbate was eluted with a 50 mM tris hydrochloride buffer solution/0.2 M NaCl/0.1 M $CaCl_2$/0.2 M benzamidine/pH 7.5. When the eluate was tested for the activity of the blood coagulant factor VIII with the synthesized substrate S-2222 (made by Daiichi Yakuhin K. K.), it was confirmed to possess activity exceeding 60%.

EXAMPLE 5

When 1000 μ of a blood coagulant factor VIII originating in human blood plasma (made by Nippon Red Cross and sold under the trademark designation of "Cross Eight M") was tested in the same manner as in Example 4, it was found to possess activity of about 60%.

EXAMPLE 6

One liter of citric acid blood plasma and 80 ml of 1 M $BaCl_2$ added dropwise thereto over a period of 0.5 hour were centrifuged (4° C., 4000×g) to obtain a precipitate. This precipitate was washed with a 50 mM phosphate buffer solution/0.1 M NaCl/5 mM benzamidine/pH 6.5 and dissolved in 0.5 liter of neat citric acid. The resultant solution and 80 ml of 1 M $BaCl_2$ added dropwise thereto over a period of 0.5 hour were centrifuged (4° C., 4000×g) and the resultant precipitate was dissolved in 0.2 M EDTA (ethylene diamine tetraacetic acid) of pH 7. Further, a 40–70% ammonium sulfate fraction of this solution was dissolved in 50 mM tris hydrochloride buffer solution/0.1 M NaCl/pH 7.5, dialyzed against the same buffer solution, and treated with dextran sulfuric acid agarose to recover a PC fraction. The PC fraction was added to a column packed with the anhydrothrombin Sepharose obtained in Example 1 and equilibrated with the same buffer solution. The adsorbate was eluted by exposure to a concentration graduation of NaCl from 0.1 M to 2 M. It was consequently confirmed that the protein C was eluted with NaCl having a concentration of about 1 M. By this method, the relative activity was raised to about 12000 times the original level and the refinement was effected with a yield of about 60%.

EXAMPLE 7

A sample obtained by treating citric acid blood plasma under the same conditions as in Example 6 until the stage of dialysis was added to a column packed with the same anhydrothrombin Sepharose as used in Example 6 and then washed with a 50 mM tris hydrochloride buffer solution/0.5 M NaCl/pH 7.5. After the peak of impurities terminated, the adsorbate was eluted with a 50 mM tris hydrochloride buffer solution/0.2 M NaCl/0.1 M benzamidine/pH7.5. By this method, the relative activity was raised to about 10000 times the original level and the refinement was effected with a yield of about 60%.

EXAMPLE 8

A blood coagulant factor V [prepared by the method reported in K. Suzuki, B. Dahlback, J. Stenflo, K. Biol. Cheml, 257, 6556 (1982)] and a blood coagulant factor XI [prepared by the method reported in B. N. Bauma, J. H. Griffin, J. Biol. Chem., 252, 6432 (1977)] were respectively added to a column packed with the same anhydrothrombin Sepharose as used in Example 1. When the blood coagulant factor V and the blood coagulant factor XI were recovered by washing the column and eluting the adsorbate by means of concentration graduation in the same manner as in Example 1, the specific activity was raised respectively to about 1.2 times and about 1.1 times the original level and the ratio of recovery was about 65% and 70%.

Industrial Applicability

This invention has originated in the discovery as a novel and inexpensive means of separation and refinement of affinity chromatography formed by using as a ligand capable of specifically and reversibly reacting with a thrombin substrate a thrombin such as, for example, anhydrothrombin deprived of nucleophilicity (activity) without causing stereostructure to the linkage with the substrate and the discovery has resulted in the perfection of a method for refinement of one thrombin substrate selected from the group of thrombin substrates owing to the incorporation of a step of the affinity chromatography in the process of the refinement. This method which resorts to a simple and expeditious procedure of separation and refinement, permits selective refinement of a thrombin substrate to be attained definitely inexpensively as compared with the method using an antiprotein C antibody with a high yield (about 60%, a level about twice the yield, about 30%, attained by the use of the antiprotein C antibody), at a high assay efficiently, safely, and stably without suffering inclusion of such impurities as a heterogenous animal protein.

This invention further allows a thrombin substrate (or two or more such substrates) suffered to be included as a foreign matter during the production (particularly refinement and separation) of preparation other than the thrombin substrate to be removed highly effectively by a procedure of elimination resorting to affinity chromatography formed by using as a ligand capable of specifically and reversibly reacting with a thrombin substrate a thrombin deprived of nucleophilicity (activity) without causing stereostructure to the linkage with the substrate, such as, for example, anhydrothrombin. Thus, this invention can be applied to a means for heightening the purity of such product of refinement as mentioned above. The present invention can provide a highly effective means for removal of a thrombin substrate in a method for refinement and separation of a wide variety of preparations.

Specifically, the method for refinement of FXIII according to this invention permits varying species of FXIII produced either naturally or by the manipulation of gene recombination to be refined with high assay at a high ratio of recovery as compared with the conventional method of refinement. It also permits effective separation and removal of such substances and viruses as form possible causes for immunogens, which are problematic for the FXIII originating in the human placenta and, consequently, allays markedly the possibility of the produced FXIII including such harmful substances. Also this method enables the FXIII of human blood plasma origin which excels in safety to enjoy further improvement in ratio of recovery and degree of refinement. This fact contributes to the effective utilization of precious blood plasma.

Further, this invention permits the FVIII to be refined inexpensively as compared with the monoclonal antibody without possibly suffering inclusion of such impurities as heterogenous animal proteins owing to the incorporation in the process of refinement of FVIII the affinity chromatography formed by using as a ligand a thrombin such as, for example, anhydrothrombin deprived of activity without causing stereostructure to the linkage with a substrate.

What is claimed is:

1. A method for refinement of a blood coagulant factor VIII characterized by incorporating therein a step of affinity chromatography formed by using an affinity adsorbent having as a ligand a thrombin or thrombin analogue deprived of nucleophilicity (activity) without affecting the stereostructure of a binding site with the blood.

2. A method for refinement according to claim 1, wherein said thrombin analogue deprived of nucleophilicity (activity) without affecting the stereostructure of a binding site with the factor VIII is a mutant of thrombin formed of an amino acid sequence having at least one of the amino acids of a thrombin depleted, substituted, or added by the manipulation of gene combination.

3. A method for refinement according to claim 1, wherein said thrombin analogue deprived of nucleophilicity (activity) without affecting the stereostructure of a binding site with the factor VIII is the anhydrothrombin which is synthesized by a process comprising:

1. a step of causing the active serine residue site of a thrombin to react with a synthesis inhibitor,
  2. a step of subjecting the resultant reaction product to an alkali treatment at a pH of not less than 11,
  3. a step of carrying out a work of recovery, and performs these steps sequentially in the order mentioned, and is characterized by allowing the presence of at least one compound selected from the group consisting of polyhydric alcohols and saccharides and a salt or an ampholeric electrolyte at least at the step for performing the work of recovery.

* * * * *